United States Patent
Wilson

[19]

[11] Patent Number: 5,772,641
[45] Date of Patent: Jun. 30, 1998

[54] OVERLAPPING WELDS FOR CATHETER CONSTRUCTIONS

[75] Inventor: James C. Wilson, Queensbury, N.Y.

[73] Assignee: Medi-Dyne Inc., Glens Falls, N.Y.

[21] Appl. No.: 570,941

[22] Filed: Dec. 12, 1995

[51] Int. Cl.⁶ .................................................. A61M 25/00
[52] U.S. Cl. ........................................... 604/280; 604/281
[58] Field of Search .................................... 604/264, 280, 604/281, 282; 128/656, 658; 138/156, 170, 171

[56] References Cited

U.S. PATENT DOCUMENTS

| | | |
|---|---|---|
| 3,924,632 | 12/1975 | Cook . |
| 3,945,867 | 3/1976 | Heller, Jr. et al. . |
| 3,962,153 | 6/1976 | Gore . |
| 3,965,909 | 6/1976 | Waddell et al. . |
| 4,044,765 | 8/1977 | Kline . |
| 4,052,989 | 10/1977 | Kline . |
| 4,305,983 | 12/1981 | Hoppe et al. . |
| 4,321,226 | 3/1982 | Markling . |
| 4,323,071 | 4/1982 | Simpson et al. . |
| 4,347,204 | 8/1982 | Takagi et al. . |
| 4,385,635 | 5/1983 | Ruiz . |
| 4,391,302 | 7/1983 | Huhn et al. . |
| 4,402,684 | 9/1983 | Jessup . |
| 4,425,919 | 1/1984 | Alston, Jr. et al. . |
| 4,430,083 | 2/1984 | Ganz et al. . |
| 4,430,282 | 2/1984 | Stack . |
| 4,430,283 | 2/1984 | Burnett et al. . |
| 4,447,239 | 5/1984 | Krütten . |
| 4,464,176 | 8/1984 | Wijayarathna . |
| 4,516,972 | 5/1985 | Samson . |
| 4,517,247 | 5/1985 | Suzuki et al. . |
| 4,531,943 | 7/1985 | Van Tassel et al. ............... 128/658 |
| 4,547,193 | 10/1985 | Rydell . |
| 4,563,181 | 1/1986 | Wijayarathna et al. . |
| 4,577,543 | 3/1986 | Wilson . |
| 4,580,790 | 4/1986 | Doose . |
| 4,596,563 | 6/1986 | Pande . |
| 4,627,844 | 12/1986 | Schmitt . |
| 4,636,346 | 1/1987 | Gold et al. . |
| 4,648,892 | 3/1987 | Kittrell et al. . |
| 4,662,404 | 5/1987 | LeVeen et al. . |
| 4,665,604 | 5/1987 | Dubowik . |
| 4,690,175 | 9/1987 | Ouchi et al. . |
| 4,764,324 | 8/1988 | Burnham . |
| 4,793,351 | 12/1988 | Landman et al. . |
| 4,813,930 | 3/1989 | Elliott . |
| 4,817,613 | 4/1989 | Jaraczewski et al. . |
| 4,836,872 | 6/1989 | Landry et al. . |
| 4,842,590 | 6/1989 | Tanabe et al. . |
| 4,861,337 | 8/1989 | George . |
| 4,863,442 | 9/1989 | DeMello et al. . |
| 4,886,506 | 12/1989 | Lovgren et al. . |
| 4,898,591 | 2/1990 | Jang et al. . |
| 4,898,702 | 2/1990 | Elkins et al. . |
| 4,899,787 | 2/1990 | Ouchi et al. . |
| 4,904,431 | 2/1990 | O'Maleki . |
| 4,925,710 | 5/1990 | Buck et al. . |
| 4,961,731 | 10/1990 | Bodicky et al. . |
| 5,005,587 | 4/1991 | Scott . |
| 5,037,404 | 8/1991 | Gold et al. . |
| 5,049,138 | 9/1991 | Chevalier et al. ........................ 604/93 |
| 5,057,092 | 10/1991 | Webster, Jr. . |
| 5,078,702 | 1/1992 | Pomeranz ............................... 604/280 |
| 5,105,819 | 4/1992 | Wollschläger et al. . |
| 5,147,315 | 9/1992 | Weber . |
| 5,156,155 | 10/1992 | King . |

(List continued on next page.)

FOREIGN PATENT DOCUMENTS

| | | |
|---|---|---|
| 0 334 640 | 9/1989 | European Pat. Off. . |
| 2 043 201 | 10/1980 | United Kingdom . |
| 2 101 680 | 1/1983 | United Kingdom . |
| 2 156 680 | 10/1985 | United Kingdom . |
| WO 95/13110 | 5/1995 | WIPO . |

Primary Examiner—Mark Bockelman
Attorney, Agent, or Firm—Nixon & Vanderhye P.C.

[57] ABSTRACT

A catheter having at least two lengths of tubular material axially joined together by a welded joint with no perceptible change in diameter at the welded joint; the welded joint including a substantial axially oriented seam between the two lengths of material.

15 Claims, 3 Drawing Sheets

U.S. PATENT DOCUMENTS

| | | |
|---|---|---|
| 5,160,559 | 11/1992 | Scovil et al. . |
| 5,171,232 | 12/1992 | Castillo et al. . |
| 5,207,960 | 5/1993 | Moret de Rocheprise . |
| 5,221,270 | 6/1993 | Parker . |
| 5,221,271 | 6/1993 | Nicholson et al. . |
| 5,234,416 | 8/1993 | Macaulay et al. . |
| 5,254,107 | 10/1993 | Soltesz . |
| 5,279,596 | 1/1994 | Castaneda et al. . |
| 5,308,342 | 5/1994 | Sepetka et al. . |
| 5,312,356 | 5/1994 | Engelson et al. . |
| 5,318,032 | 6/1994 | Lonsbury et al. . |
| 5,336,205 | 8/1994 | Zenzen et al. . |
| 5,348,536 | 9/1994 | Young et al. . |
| 5,358,493 | 10/1994 | Schweich, Jr. et al. . |
| 5,387,199 | 2/1995 | Siman et al. . |
| 5,401,257 | 3/1995 | Chevalier, Jr. et al. ................ 604/280 |
| 5,403,292 | 4/1995 | Ju . |
| 5,441,489 | 8/1995 | Utsumi et al. . |
| 5,445,624 | 8/1995 | Jimenez . |
| 5,542,937 | 8/1996 | Chee et al. .............................. 604/280 |
| 5,545,151 | 8/1996 | O'Connor et al. ...................... 604/282 |
| 5,571,073 | 11/1996 | Castillo ................................... 604/282 |
| 5,584,821 | 12/1996 | Hobbs et al. ........................... 604/282 |

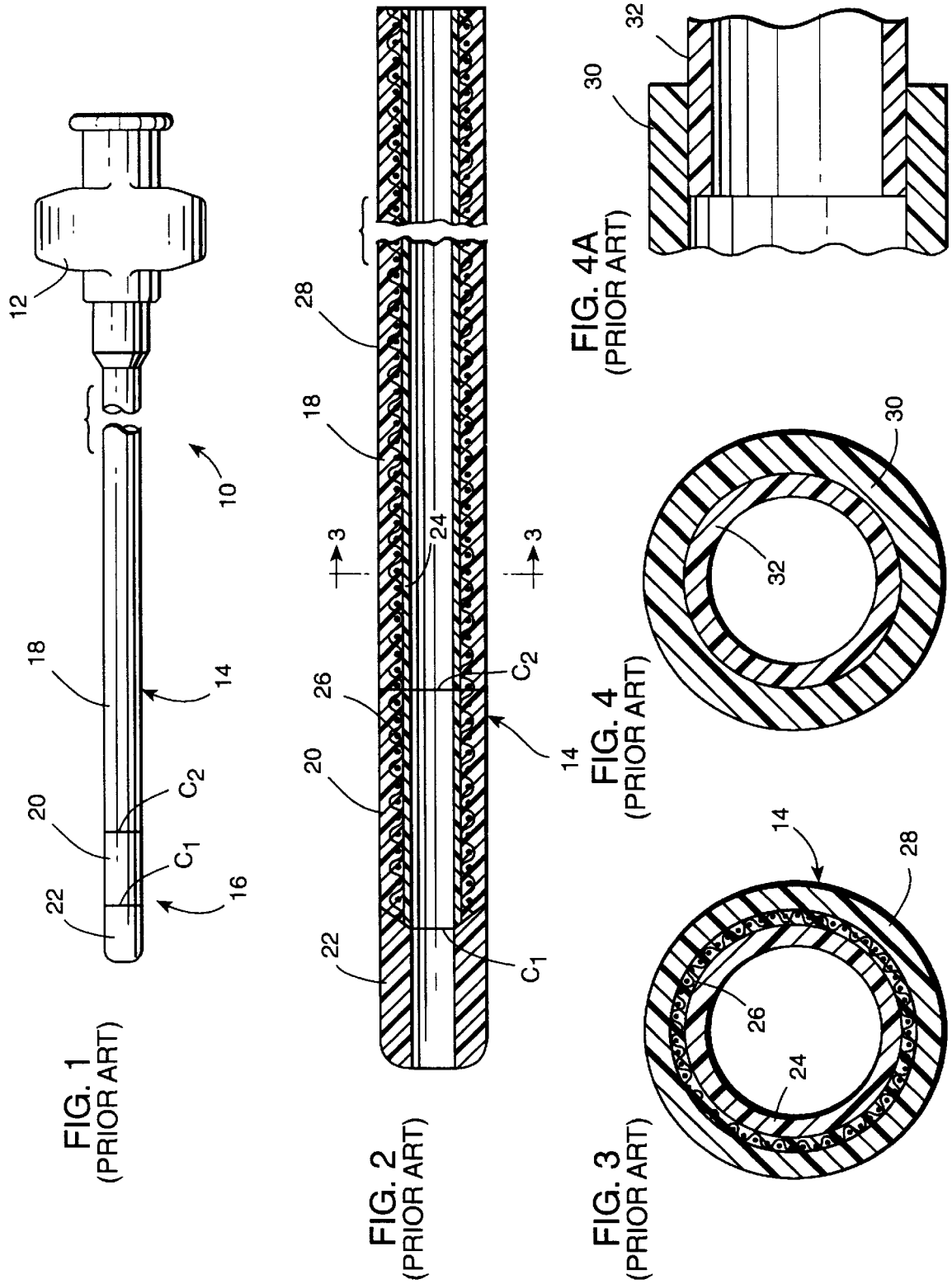

5,772,641

OVERLAPPING WELDS FOR CATHETER CONSTRUCTIONS

This invention relates generally to catheter constructions, and more particularly to welded joints between adjacent lengths of catheter material.

BACKGROUND AND SUMMARY OF THE INVENTION

Currently, both diagnostic and therapeutic catheters are manufactured by forming braided tubes of stainless steel fibers or strands, over a mandrel. More specifically, the braided tube may be formed about an inner Teflon® liner or tube initially carried on a supporting mandrel. An outer plastic layer may then be extruded about the braided material to create the catheter body. Current catheter constructions also utilize a transition tip which is not reinforced with braid in order that the tip be softer and more flexible than the remaining portions of the catheter. In some catheter designs, an even more flexible tip is bonded to the free end of the tubular transition tip.

Catheters which incorporate multiple axial sections typically employ butt or lap weld joints to secure the axial sections of the catheter together. See, for example, U.S. Pat. Nos. 5,254,107; 4,861,337; 4,793,351; 4,662,404; and 4,391,302.

Catheters incorporating either butt or lap type welded joints are not completely satisfactory however, and it is thus the object of this invention to improve upon prior catheter constructions by incorporating unique weld configurations which have a substantial axial seam component extending along the axis of the catheter. In other words, adjacent catheter sections are cut and welded in such away that they overlap in the longitudinal direction, but without altering the outer diameter of the catheter. This arrangement not only increases surface area at the weld joints and thereby also increases bond integrity, but also creates a more desirable transition between the same materials of different durometer or different materials with or without the same durometer, than other more conventional welds such as lap or butt welds.

The unique weld configurations of this invention also permit alteration of properties or characteristics of the catheter material in the area of the weld, and this feature is particularly advantageous in areas of the catheter that will be curved, in that different stiffness or hardness materials can be used on the inside and outside of the curve.

Examples of the unique weld configurations in accordance with this invention include step joints, taper joints, and combinations of the two.

Thus, in accordance with its broader aspects, the present invention relates to a catheter having at least two lengths of tubular material axially joined together by a welded joint with no perceptible change in outer diameter at the welded joint; the welded joint including a substantial axially oriented seam between the two lengths of material.

In another aspect, the invention relates to a catheter having at least two lengths of tubular material axially joined by a welded joint, the welded joint having an axial length component of at least 0.5 cm. in length, and preferably in the range of 0.5–10 cm.

Other objects and advantages of the subject invention will become apparent from the detailed description which follows.

BRIEF DESCRIPTION OF THE DRAWINGS

FIG. 1 is a side elevation, partly broken away, of a conventional catheter construction;

FIG. 2 is a side section of the distal end of the catheter shown in FIG. 1;

FIG. 3 is a section taken along the line 3—3 of FIG. 2;

FIG. 4 is a cross section of a conventional lap weld in a catheter;

FIG. 4A is a partial side section of the welded joint illustrated in FIG. 4;

DETAILED DESCRIPTION OF THE DRAWINGS

Figure 5:
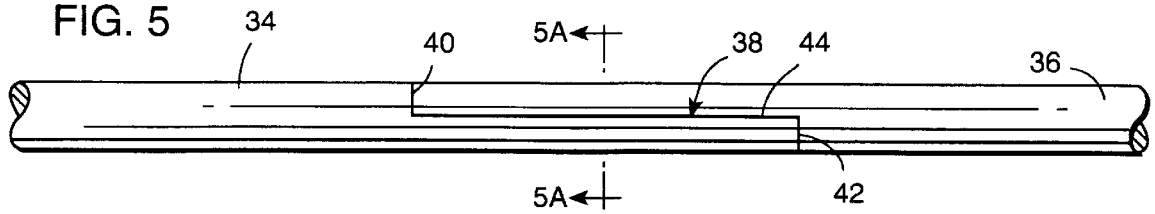
FIG. 5 is a side elevation of a catheter incorporating a step weld in accordance with the present invention.

FIGS. 1 and 2 represent a known catheter construction of the type disclosed in U.S. Pat. No. 5,254,107. The catheter assembly 10 includes a conventional hub 12 at its proximal end, and a tubular catheter 14 extending from the hub 12 to a distal end 16. The catheter may have a first axial section 18, a second axial section 20 and a distal tip section 22.

The catheter 14 comprises an inner tubular plastic layer 24, which may be made of fluoro polymers such as PTFE, FEP or other similar polymers. A second layer 26 comprises a braided stainless steel tube applied by a conventional braiding machine. An outer, third layer 28 of plastic is then applied by suitable means over the braided layer. As disclosed in the '107 patent, this outer layer may include two or more axial sections. For example, the first axial section 18 may be made of a plastic material such as nylon 12 with a Shore D durometer of about 65–70. The second axial section 20 may be Pebax, but may have a Shore D durometer of about 35–55. The transition tip 22 may be Pebax and may or may not be reinforced by the braided layer 26. In the '107 patent, the adjacent axial sections are butt welded or fused together, such that the joints describe circles C1 and C2 perpendicular to the longitudinal axis of the catheter.

The present invention relates to new and unique weld configurations for joining axial sections of the outer plastic layer of a catheter as generally described above.

Conventional welds used in catheter constructions are either of the butt type shown in FIGS. 1 and 2, or of the overlapping variety, typically known as "lap" welds as shown in FIGS. 4 and 4A (inner layer and braided layer removed for the sake of clarity). Thus, one tubular portion 30 is received over a second tubular portion 32 and welded thereto, such that, in the weld area, a double thickness is created, as best seen in FIG. 4A.

Figure 5A:
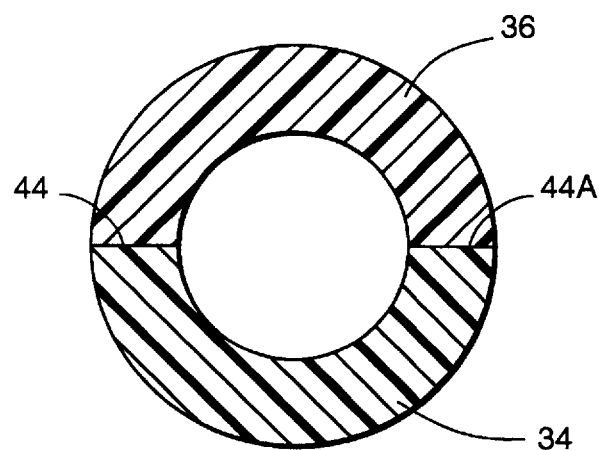
FIG. 5A is a section taken along the line 5A—5A of FIG. 5.

In accordance with this invention, welds as shown in figures 5–10 are used to connect lengths of catheter tubing, which welds are designed to have substantial axial length, but without altering the outer diameter of the catheter. With the exception of FIG. 10, the adjacent catheter sections are substantial mirror images of each other at the joint interface, with external seams having substantial axial components. Thus, each of the adjacent lengths each form substantially half of the peripheral surface of the catheter along the welded joint. In FIG. 5, for example, a first catheter length 34 is connected to a second catheter length 36 by a step weld 38 which includes radial seam portions 40 and 42 and extended axial seam portions 44, 44A (see FIG. 5A). Note there is no double thickness of material and no change in outside diameter. Note also that the seam lies along the wall thicknesses of the adjacent sections as shown in FIG. 5A. Here again, internal layers have been omitted simply for the sake of clarity.

Figure 6:
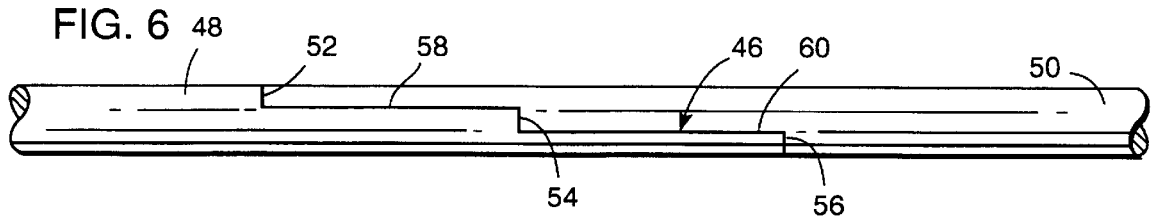
FIG. 6 is a side elevation of a catheter incorporating a multi-step weld in accordance with the invention.

In FIG. 6, a multi-step weld 46 axially joins catheter lengths 48 20 and 50, with the weld having three radial seam portions 52, 54 and 56 and two extended axial seam portions 58 and 60.

Figure 7:
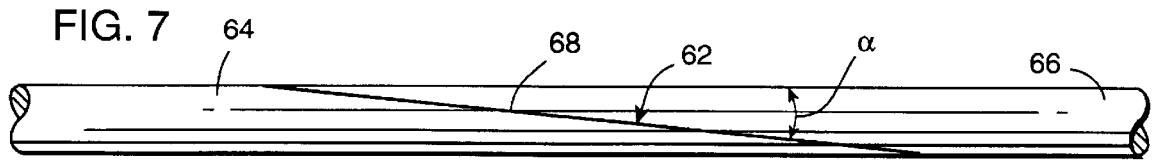
FIG. 7 is a side elevation of a catheter incorporating a shallow angle weld in accordance with the invention.

In FIG. 7, a shallow angle weld 62 axially joins catheter lengths 64 and 66. While no purely radial weld seam portions are formed in this arrangement, a single extended axial portion 68 gradually transitions along a shallow angle α, i.e., seam portion 68 is angularly inclined in the longitudinal direction, relative to the longitudinal axis of the catheter.

Figure 8:
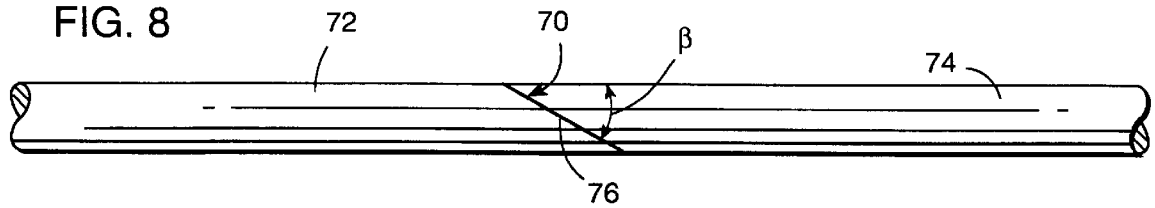
FIG. 8 is a side elevation of a catheter incorporating a steep angle weld in accordance with the invention.

FIG. 8 illustrates a variation in the weld configuration of FIG. 7, in that the weld 70 axially joining catheter lengths 72, 74 axially along a seam 76 which in the longitudinal direction of the catheter, makes a relatively steep angle β, relative to the axis of the catheter.

Figure 9:
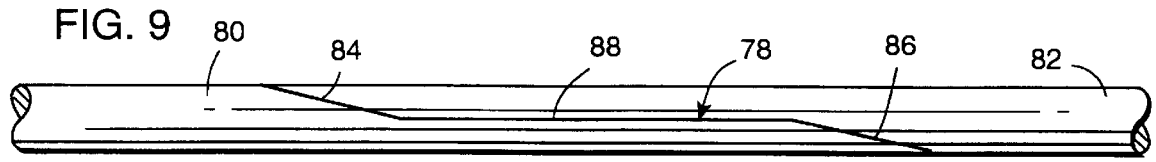
FIG. 9 is a side elevation of a catheter incorporating a combination step/angle weld in accordance with the invention.

FIG. 9 illustrates a hybrid weld 78 axially joining catheter lengths 80, 82 along a pair of angled or inclined seams 84, 86 connected by an extended axial seam 88.

Figure 10:
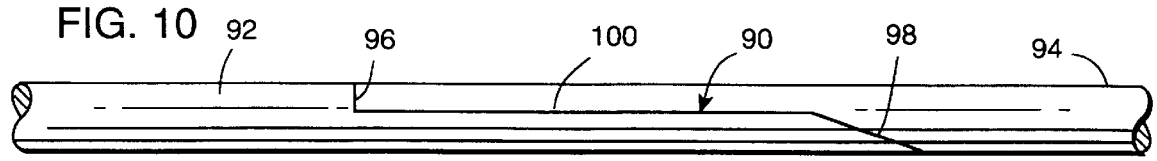
FIG. 10 is a side elevation of a catheter incorporating a combination step, angle and butt weld in accordance with the present invention.

FIG. 10 illustrates yet another hybrid weld 90 axially joining 10 catheter lengths 92, 94. The weld includes a radial seam portion 96 and an angled or inclined seam portion 98 connected by an extended axial seam portion 100.

In each instance, the above described welds axially join two lengths of catheter with a significant axial seam portion (at least about 0.5 cm. in axial length and preferably 0.5–10 cm.) but without altering the outside diameter (OD) of the catheter. In other words, the OD of the outer plastic layer does not change and, in no case are there double thicknesses as in lap welds. At the same time, unlike butt welds, the weld seams extend axially along the length of the catheter. These extended axial portions of the various weld configurations (the longitudinal or axial extent of which may be varied) allow the catheter to be constructed with certain desired properties or characteristics as explained below.

The overall increased surface area of the welded joints increases the bond integrity between the two joined sections. The various weld configurations also create more desirable transitions between materials of different durometers, resins, etc. than typical butt or lap welded joints.

Figure 11:
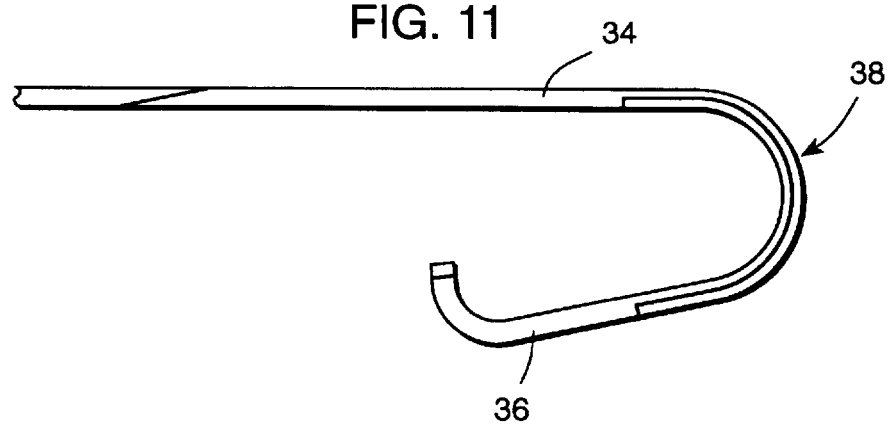
FIG. 11 is a partial side elevation illustrating a catheter with multiple sections including a curved section incorporating a weld in accordance with the subject invention.

It is also possible to vary the characteristics of the catheter along its length by means of the overlapping welds described herein. For example, for the catheter shown in FIGS. 5 and 5A, with an axially extended overlap of from, e.g., 0.5 to 10 cm., a unique section of catheter is created where section 34 might be a hard durometer (e.g., 60–70 D Scale) and section 36 a soft durometer (e.g., 25–50 D Scale or even a very soft shore A hardness), the combined axial section along the axial length of the weld has a stiffness which is the average of the two durometers. This ability to create lengths of catheter with different 10 properties or characteristics is most advantageous in areas of the catheter which will incorporate (or be bent into) curved areas. With reference now to FIG. 11, which illustrates the catheter sections 34 and 36 in a curved state through the weld area 38, the length 34 has a harder durometer—on the outside of the curve; while the length 36 has a softer durometer—on the inside of the curve. As a result, not only does the weld overlap area have a desirable stiffness which falls between the stiffness of the materials used to form sections 34 and 36, but in addition, unique curve retention properties are created by reason of the dominance of the harder durometer over the softer durometer. This is merely one example of the many possible applications of the concept. It is quite possible, for example, that for a similar curved area with a different purpose, the softer durometer may be on the outside and the harder durometer on the inside of the curve. By altering the radial location of the axial seam of the weld, different percentages of harder and softer durometers can be employed. As a visual aid to distinguish catheter sections having different properties, the axially overlapping sections may be color coded.

It should also be pointed out that the different catheter lengths can be of the same material (e.g., suitable resins) but have different durometers, or they can be of different materials of the same or different durometer. Suitable resins include Nylon 11 and Nylon 12; Pebax (25D to 70D); Nylon/Pebax blends; polyurethanes (large Durometer—infinite range); polyethylenes (high and low density); PVC; and other medical grade resins and various combinations of same.

Typical catheter constructions as shown and described herein may be in the size range of 1–15 French (0.013" to about 0.200" I.D.).

One or more inner layers (omitted from FIG. 5A but similar to FIG. 3) may include, for example, a conventional PTFE, FEP or similar liner reinforced by stainless steel braid. The invention here is applicable, 15 however, to a wide range of catheter types. For example, both diagnostic (angiography) and therapeutic (guiding) catheters (and other catheter technologies such as PTA, PTCA, electrophysiology, pacing leads, etc.) are suitable candidates for incorporation of the welds of this invention. Such catheters, as indicated above, may or may not include woven or braided reinforcements. Such reinforcements, if used, may comprise metal or synthetic materials including stainless steel, Kevlar®, etc. The catheters may be of single or multi-lumen design and may or may not have a Teflon® or other friction reducing lining. The catheters may or may not have a tapered distal portion and may or may not have side ports. While the catheter constructions illustrated herein show only a single weld per catheter, i.e., two axial sections, it should be understood that each catheter may have more than one welded area and may incorporate two or more different resins with the same or varying durometers.

With regard to the weld areas per se, the transition portions, i.e., the axially extending portions of the weld, may have an axial length to radial depth ratio of from about 3:1 to about 40:1. For purposes of discussion herein, a short transition weld has a ratio of about 3:1 to about 12:1, whereas a long transition weld has a ratio of about 12:1 to about 40:1. Short transition welds provide increased surface areas which strengthens the welded joints, and provide longer, less abrupt transition areas than simple butt welds. Such welds minimize the tendency of kinking and provide better torque transmission characteristics than conventional butt welds.

Long transition welds also provide increased surface area for strengthening the welded joints. In addition, long transition welds produce more desirable feel and/or handling characteristics in use. The orientation of different materials in long transition welds provides ease of straightening and permits unique properties to be established within one or more curved areas of the catheter. Long transition welds also allow for greater differences in durometer.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and cope of the appended claims.

What is claimed is:

1. A catheter having at least two adjacent lengths of tubular material axially overlapped and joined together by a welded joint, said lengths having substantially identical and uniform outer diameters at and adjacent the welded joint; the catheter having a continuous external peripheral surface and a lumen extending along a longitudinal axis, and the welded joint including a seam on said external peripheral surface, at least a portion of said seam extending parallel to said longitudinal axis in between the two lengths of material such that each of said at least two adjacent lengths form substantially half of the peripheral surface of the catheter along the welded joint.

2. The catheter of claim 1 wherein said axially oriented external seam is flanked on either side thereof by radial portions extending substantially perpendicular to said longitudinal axis.

3. The catheter of claim 1 wherein said axially oriented seam is connected into a pair of axial sections divided by a radial portion.

4. The catheter of claim 1 wherein said axially oriented external seam is parallel to said longitudinal axis and is flanked at either end thereof by inclined portions extending angularly relative to said longitudinal axis.

5. The catheter of claim 1 wherein said two lengths of tubular material comprise two different materials.

6. The catheter of claim 1 wherein said two lengths of tubular material have different durometers.

7. The catheter of claim 6 wherein said two lengths of tubular material are constructed of the same material.

8. The catheter of claim 1 wherein said two lengths of tubular material are color coded.

9. A catheter having a peripheral surface and a lumen extending along a longitudinal axis and at least two lengths of tubular material axially joined by a welded joint, said at least two lengths having substantially identical outer diameters, said welded joint having a seam portion along said peripheral surface parallel to said longitudinal axis at least 0.5 cm in length.

10. The catheter of claim 9 wherein said axial length component has a length of between 0.5 and about 10 cm.

11. The catheter of claim 10 wherein said two lengths of tubular material comprise different resins having dissimilar durometers.

12. The catheter of claim 11 wherein said two lengths of tubular material comprise an outer layer of said catheter and wherein said catheter includes a reinforced inner liner.

13. A catheter having a peripheral surface and a lumen extending along a longitudinal axis and having at least two lengths of tubular material axially joined together by a welded joint defined by an external seam on said peripheral surface, a portion of said seam extending parallel to said longitudinal axis wherein adjacent sections partially overlap in an axial direction but without change in said outer diameters in the partially overlapped area, and wherein a ratio of weld axial length to said radial depth is from about 3:1 to about 40:1.

14. An intravascular catheter having a peripheral surface and a lumen extending along a longitudinal axis which comprises:

a flexible, plastic inner tube; a fibrous, tubular reinforcement member carried by said inner tube and an outer tube; and an outer tube of substantially constant outer diameter including a first axial section comprising a first plastic material overlying said inner tube and reinforcement member;

a second axial section comprising a second plastic material having different physical properties from said first plastic material and overlying said inner tube and reinforcement member, wherein said first and second axial sections are substantial mirror images of each other; and a welded joint between said first and second axial sections, said welded joint including a seam portion on said peripheral surface at least 0.5 cm in length extending parallel to said longitudinal axis.

15. A catheter having a peripheral surface and a lumen extending along a longitudinal axis and having at least two longitudinally overlapped lengths of tubular material axially joined together by a welded joint, said lengths having substantially identical outer diameters, and wherein said lengths are substantially mirror images of each other in areas corresponding to said welded joint, and further wherein said lengths are joined along external seams on said peripheral surface, at least one of said seams having a portion extending parallel to said longitudinal axis of said lumen.

* * * * *